United States Patent
Pellinat

(10) Patent No.: US 7,287,017 B2
(45) Date of Patent: Oct. 23, 2007

(54) DECISION ENGINE

(75) Inventor: Martin Pellinat, San Diego, CA (US)

(73) Assignee: Igego Methodologies, Inc., San Diego, CA (US)

( * ) Notice: Subject to any disclaimer, the term of this patent is extended or adjusted under 35 U.S.C. 154(b) by 486 days.

(21) Appl. No.: 10/845,301

(22) Filed: May 13, 2004

(65) Prior Publication Data

US 2004/0220834 A1 Nov. 4, 2004

Related U.S. Application Data

(63) Continuation-in-part of application No. 09/834,779, filed on Apr. 12, 2001, now Pat. No. 6,917,928.

(51) Int. Cl.
G06F 17/00 (2006.01)
G06N 7/00 (2006.01)
G06N 7/08 (2006.01)

(52) U.S. Cl. ........................................ 706/59
(58) Field of Classification Search ................... 706/59
See application file for complete search history.

(56) References Cited

U.S. PATENT DOCUMENTS

| | | | | |
|---|---|---|---|---|
| 5,172,313 A | 12/1992 | Schumacher | ................ | 364/401 |
| 5,392,382 A | 2/1995 | Schoppers | .................... | 395/10 |
| 5,835,758 A | 11/1998 | Nochur et al. | ............... | 395/613 |
| 5,873,071 A | 2/1999 | Ferstenberg et al. | | |
| 5,903,453 A | 5/1999 | Stoddard II | .................. | 364/184 |
| 5,954,510 A | 9/1999 | Merrill et al. | ............... | 434/236 |
| 6,144,953 A * | 11/2000 | Sorrells et al. | ................ | 706/60 |
| 6,322,366 B1 | 11/2001 | Bergan et al. | ............... | 434/118 |
| 6,338,628 B1 | 1/2002 | Smith | ......................... | 434/236 |
| 6,421,655 B1 | 7/2002 | Horvitz et al. | ................ | 706/61 |
| 6,439,893 B1 | 8/2002 | Byrd et al. | .................. | 434/236 |
| 6,442,527 B1 | 8/2002 | Worthington | ................... | 705/8 |
| 6,618,723 B1 | 9/2003 | Smith | ......................... | 707/236 |
| 6,643,385 B1 | 11/2003 | Bravomalo | .................. | 382/100 |
| 2002/0145626 A1 | 10/2002 | Richards et al. | | |

* cited by examiner

*Primary Examiner*—Anthony Knight
*Assistant Examiner*—Michael B. Holmes
(74) *Attorney, Agent, or Firm*—Hogan & Hartson LLP

(57) ABSTRACT

A software-based decision engine implements a comparative or opportunity based decision making methodology. A user selects or provides options and influencing factors. The importance of each influencing factor, and the reason for each factor's importance, is obtained. Each factor for each option is weighted, and any extra effort associated with a particular option is assessed. Resources and on-line links may be provided to assist in weighting factors. The factors may be pre-weighted based on quantifiable information. The options are ranked and displayed in a scorecard format, wherein the importance, reason and weight behind each factor of each option is displayed to the user, providing the user with quantifiable knowledge that he/she has made the best decision based on all available options and associated factors. Steps for developing an action plan to make a chosen option a reality may also be provided.

20 Claims, 6 Drawing Sheets

DECISION ENGINE

RELATED APPLICATION

This application is a continuation-in-part of commonly-owned and -invented U.S. patent application Ser. No. 09/834,779, entitled "System and Method for Personal Development Training", filed on Apr. 12, 2001 now U.S. Pat. No. 6,917,928.

FIELD OF THE INVENTION

The present invention relates to decision making and, in particular, relates to a software-implemented decision engine for providing assistance in making a decision.

BACKGROUND OF THE INVENTION

Decisions are an inevitable part of life, and many have critical impact. Decisions are made every day, some with great thought and others spontaneously. Virtually all, however, are in our control and have an effect on the direction our lives take, as well as an impact on the world around us. Therefore, for every decision-making situation, it is important to make the most informed decision possible with all of the information available at that moment for that situation.

In April 2001, the present inventor filed parent application Ser. No. 09/834,779 directed to a software-based methodology for personal use in life decision making. The methodology incorporated an algorithm, subsequently named "Weighted Inverse Perspective" (WIP), whereby users are encouraged to answer each question of the decision-making process with free expression, which then drives the questions in the following steps. The WIP algorithm captures the human element in the process of decision making by equally focusing on the factors that make up the situation, along with the reasons and driving forces behind those factors and the overall impact on each possible outcome. Upon completion of the process, the user has exhausted and uncovered all obstacles and supporting factors for the given situation, documented all possible perspectives from the outside-in, and has been guided to reach inside themselves to develop creative solutions for overcoming obstacles that can be effectively implemented.

Since the filing of the parent application, the present inventor has continued research and development, focusing on comparative- and opportunity-based aspects of the decision-making process. In particular, in consumer-oriented decisions, such as deciding which product to buy or deciding which clinical treatment path to take, for example, consumers often experience "buyer's remorse" after a purchase is made or course of treatment decided on. This is often the result of a decision made without full consideration being given to all available options and factors associated with those options. For such decision-making scenarios, there is a need for a mechanism or methodology that empowers consumers in their decision process and allows them to move forward with a purchase or other conclusive decision with confidence and knowledge that they have "sold themselves" based on a complete analysis of the information at hand.

SUMMARY OF THE INVENTION

The present invention provides a software-based decision making engine that assists one in collecting all options and factors available for a given decision, such as a product purchase or selection of a clinical treatment, and processing that information thoroughly and strategically to present the user with a ranking of the available options.

One embodiment of the invention is a software-based method for decision-making. The method comprises obtaining options to be considered for the outcome of the decision; obtaining influencing factors in making the decision; obtaining a rating of the importance of each of the influencing factors; obtaining a weighting of each of the influencing factors for each of the options; and computing and displaying a ranking of the options.

Another embodiment of the invention is a computer program product for assisting a user in making a product purchase decision. The computer program product comprises instructions for obtaining a selection of products to be considered for purchase; obtaining a selection of influencing factors in the purchase; obtaining a rating of the importance of each of the influencing factors; obtaining a reason that each of the influencing factors is important; obtaining a weighting of the factors for each option, and providing resources to assist a user in the weighting; computing and displaying a ranking of the products by multiplying the importance of each factor by its weighting and adding the results for each of the options; and providing the option to purchase the products.

Another embodiment of the invention is a computer program product for assisting a patient in making a decision between clinical treatment options. The computer program product comprises instructions for obtaining a selection of clinical treatment options to be considered; obtaining a selection of influencing factors in the decision; obtaining a rating of the importance of each of the influencing factors; obtaining a reason that each of the influencing factors is important; obtaining a weighting of the factors for each option, and providing resources to assist a user in the weighting; and computing and displaying a ranking of the clinical treatment options by multiplying the importance of each factor by its weighting and adding the results for each of the options.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Overview

Figure 1:
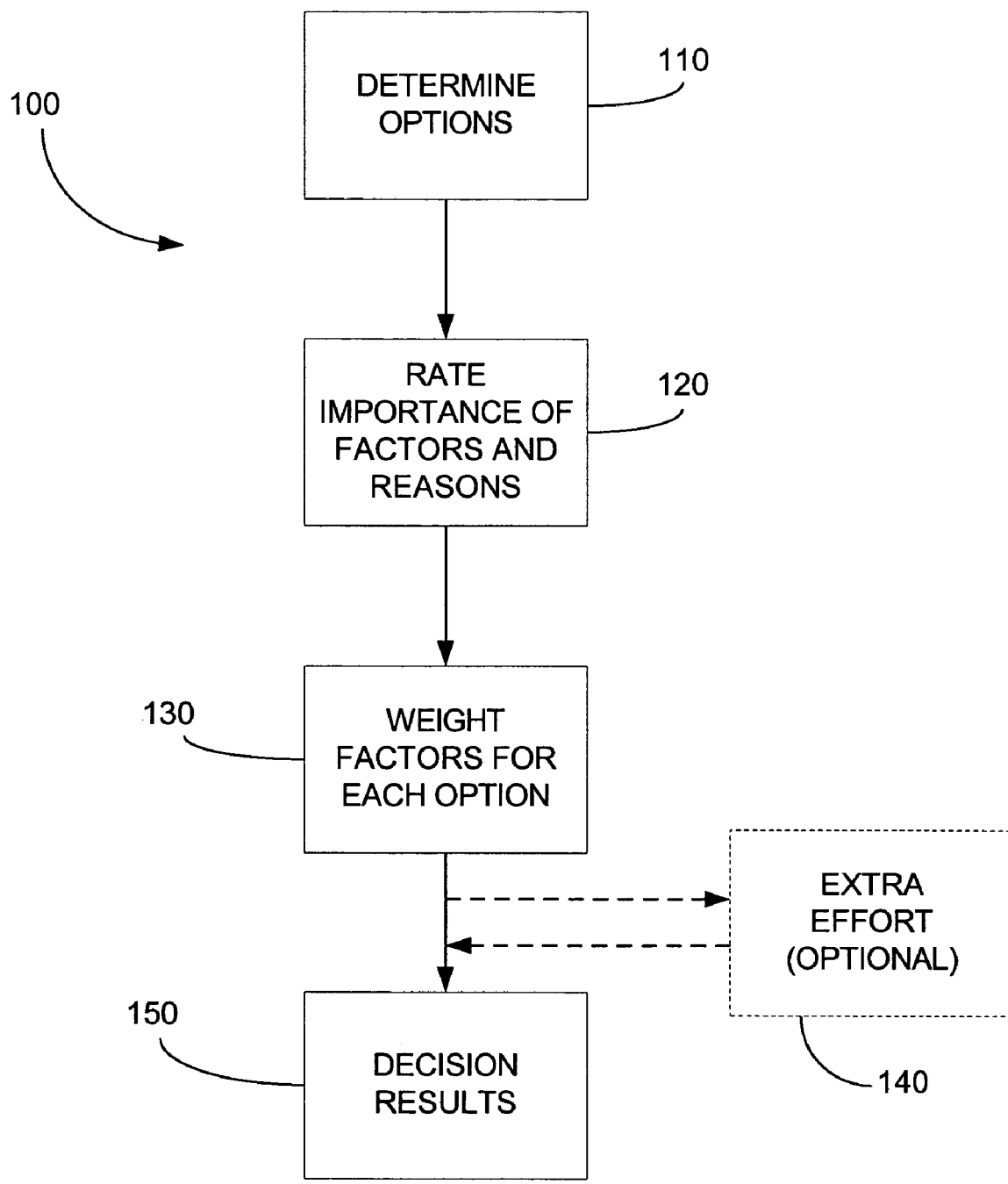
FIG. 1 is a high-level overview flow diagram of software-based decision engine according to the present invention.

An overview of decision engine 100 is presented in FIG. 1. The methodology of decision engine 100 is implemented as a computer program in a computer-readable medium, such as software, and is provided to end users to assist in their decision-making process. The software may be embodied in any number of formats including, without limitation: CD-ROMS or other storage media for purchase from retail locations or websites; as part of a software bundle pre-loaded onto the desktop of a purchased computer system; on a server website that is accessible by users via the Internet; or on a stand-alone computer station or kiosk made available to users.

Decision engine 100 has many potential applications. One important application is in the context of assisting a consumer (or business) in making a product purchase decision. This application is particularly useful where there are multiple products of the same type and serving the same need (i.e. computers, cameras, printers, televisions, automobiles, appliances, shoes, and virtually any other type of merchandise). Another application, for example, is assisting a patient in making a clinical treatment decision for elective clinical procedures. While decision engine 100 is described primarily in the environments of product purchase and patient treatment decisions, this is for exemplary purposes only and is not intended to be limiting. Decision engine 100 may be useful and incorporated in many other applications.

Decision engine 100 implements a comparative or opportunity based decision making methodology. Direct user input in selecting the options and influencing factors of a decision is obtained in step 110. A user may select, for example, a number of computer laptop models for comparison. The user also selects factors associated with the options that will affect the decision. For computer laptops, for example, the user may select factors such as size, performance, battery life, etc. The importance of each influencing factor, and the reason for each factor's importance, is obtained in step 120. The user may rate size as very important, for example, and provide the reason of a long walk to school. In step 130, each factor for each option is weighted in terms of its support for the choice of that option. Hence, the size factor for a very light laptop option might be weighted as "very supportive" while a very heavy laptop option might be rated as "not supportive". Optionally, any extra effort associated with a particular option is assessed in step 140.

In step 150 the options are ranked and displayed based on the user's input in the previous steps. In one implementation, the options are ranked and displayed in a "scorecard" format, wherein the importance, reason and weight behind each factor of each option is displayed to the user, providing the user with quantifiable knowledge that he has made the best decision based on all available options and associated factors. This empowers the user and enables him or her to make a confident purchase without being afflicted by the "buyers' remorse" that often accompanies a hasty or uninformed purchase decision.

In the application of healthcare treatment decisions, several additional advantages are provided. The patient feels confident in the treatment pathway he/she has chosen and the decision-making process supports a healthy dialogue in the patient/physician relationship. From the clinic's point of view, providing an implementation of decision engine 100 for the use of its patients in choosing between clinical options is an additional method of supporting informed consent, and also helps to establish quality healthcare measures and recognition such as "Center of Excellence" status. Finally, as discussed in more detail below, the collection and storage of decision-making data input by patients provides a way to evaluate research and resource direction by institutions, particularly in academic settings were a spectrum of treatment options are traditionally available.

The benefits and advantages provided by decision engine 100 in product purchase and clinical treatment decision applications are equally applicable in any other application where a decision among multiple options is required. These may include, without limitation, educational decisions (i.e. what college to attend), career decisions (i.e. which job to take), professional decisions and retirement decisions.

Each step of decision engine 100 is now described in greater detail.

Step 1: Determine Options and Influencing Factors

Figure 2:
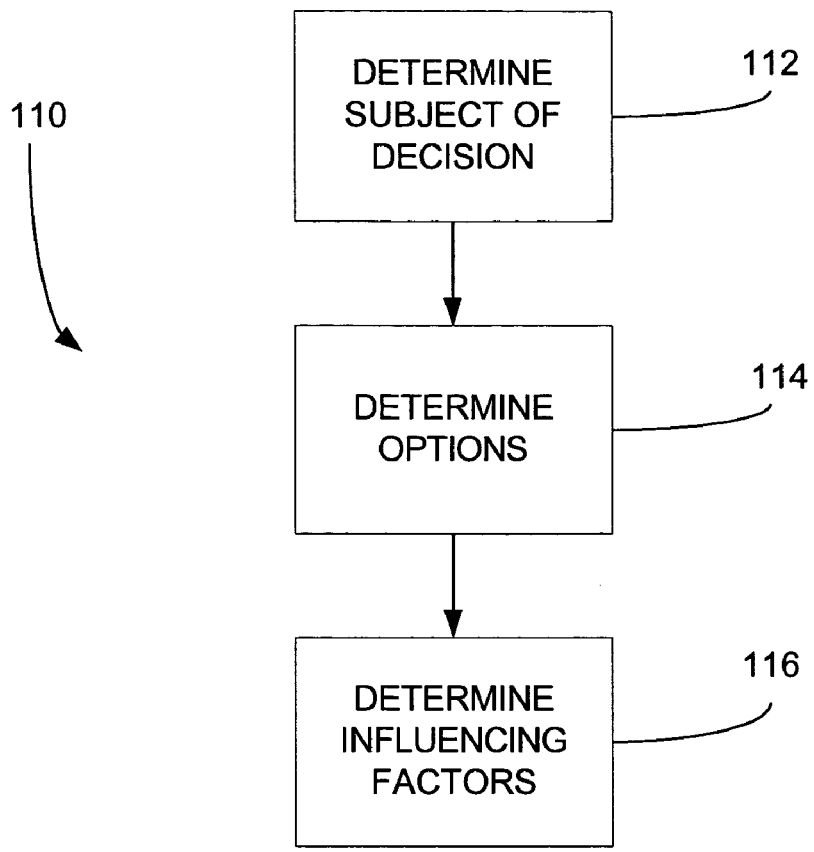
FIG. 2 is a detailed flow diagram of one aspect of the decision engine of FIG. 1 wherein options and influencing factors are determined.

The sub-steps 112-116 of step 110, obtaining the options and influencing factors from the user, are illustrated in more detail in FIG. 2. In applications not limited to a particular type of decision, the first step 112 is to determine the subject of the decision. In other words, the user is asked what it is that he/she is trying to decide. The user will be prompted to enter this information either as a free-form expression (i.e. "which car to buy"), or as a selection from a pre-defined list from a pull-down menu or the like. In an application directed to a particular computer manufacturer or to computer products in general, for example, the user may select from a list of entries such as "which laptop to buy", "which printer to buy", "which monitor to buy", and so on. In another example, the application might be used in conjunction with an on-line retailer such as Amazon.com and provide selections in step 112 such as "which book to buy", "which DVD to buy" and so on.

Where decision engine 100 is intended for a very specific decision, such as "which laptop to buy", step 112 may not be necessary. That is, where the application is presented specifically for making a single type of decision, the method may begin with step 114, where the user determines or selects his/her possible options (the possible outcomes of the decision). In the case of laptops, for example, the user may be presented with a list or menu of available laptops and asked to indicate those which he/she would like to consider as options for purchase. The options may be displayed along with links to information about each option and, where appropriate, photos of the options. Where the application is geared to a specific manufacturer, the options may be limited to that manufacturer's products. Where an entire genre of products is being considered without regard to manufacturer, the pool of options may be much larger and include those of many manufacturers. Decision engine 100 may retrieve and display options from a database or other storage medium. Finally, the user may have the option of entering an option as a free form expression, i.e., he/she may include an option other than those presented.

Decision engine 100 may also be implemented in a healthcare application to assist a patient in making a choice between different treatment options. For many conditions, patients face radically different treatment options that vary in invasiveness and morbidity, among other things. A patient with prostate cancer, for example, typically has treatment options including prostatectomy, brachytherapy, cryotherapy, radiation therapy, or no treatment at all. Hence, in step 114, the patient would select which of these options he/she would like to include in the decision-making process. In another example, a patient with the condition of arteriovenous malformation may have treatment options including surgery, embolization, radiosurgery, or no treatment at all.

Next, in step 116, the user determines or selects those factors that will influence his/her decision. These factors may be suggested by decision engine 100 based on the type of decision that is being made. If a laptop purchase decision is being made, for example, factors such as size, battery life, performance, home use, business use, network connectivity, etc. may be presented. In another example, if a prostate cancer treatment decision is being made, influencing factors may include recovery time, pain, likelihood of success and quality of life. The influencing factors may be retrieved from a common database of typical factors/features that the options in question share. Factors may also be sub-divided into groups such as "popular" features, "unique" features, etc. The user may also provide his/her own factors. A text entry box labeled as "other" or "personal", for example, may be provided where the user can enter an option as free form expression.

Step 2: Rate Importance of Factors and Obtain Reasons

Figure 3:
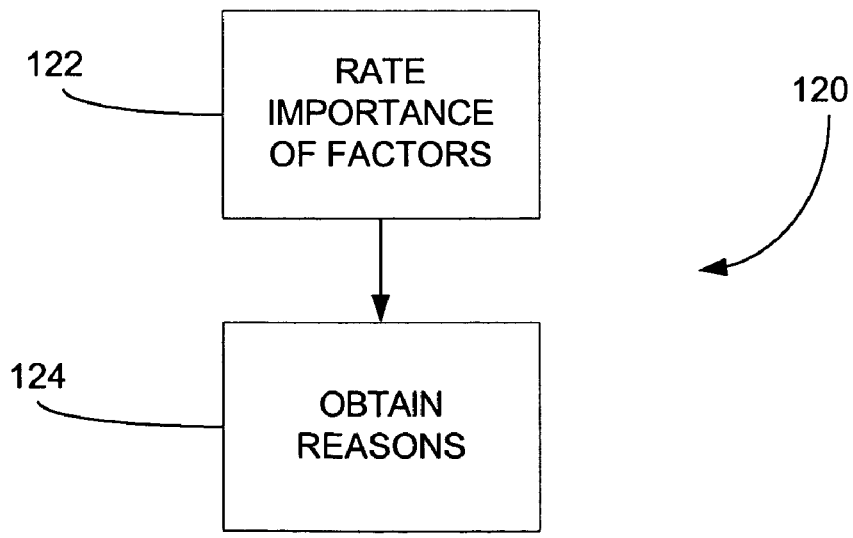
FIG. 3 is a detailed flow diagram of another aspect of the decision engine of FIG. 1 wherein the importance of factors is rated and reasons are obtained.

The sub-steps 122-124 of step 120, rating the importance of the factors and obtaining reasons, are illustrated in more detail in FIG. 3. In step 122, the user rates the importance of each factor to his/her decision. In one embodiment, the user is presented with a sliding scale that is movable using a mouse between the extremes of "not important" and "important". Alternatively, any other appropriate indicators of relative importance could be used. Depending on where the user places the scale, each factor will be assigned by decision engine 100 an integer score ranging from 0 (not important) to 10 (important). Alternatively, the user could simply be asked to numerically rank the importance of each factor on a scale from 1 to 10, or on any other useful or desired scale of scores.

In step 124, for each factor, the user is asked to enter a reason(s) that the factor is important in the decision. Referring again to the laptop scenario, for the factor "audio", the user may enter "like to listen to music while working". In the scenario of a car purchase decision, a user might pair a high importance ranking given to a "size" factor with the reason "needs to be large enough to accommodate dogs". For a clinical treatment decision, the user might enter "need to get back to work" as the reason for the importance of the factor "recovery time". The information obtained in this step is displayed to the user later along with the decision results, and serves as a reminder of how the decision was made as well as a reinforcement that the decision is sound. Additionally, the thought process that the user necessarily undertakes while considering the reason may lead him to make a more accurate ranking of the importance of the factor.

Finally, it should be noted that while step 124 provides a valuable contribution to the decision-making process, it may be omitted in some implementations. In streamlined iterations of decision engine 100 intended to generate a very quick decision, for example, step 124 might be omitted.

Step 3: Weight Factors for Each Option

Figure 4:
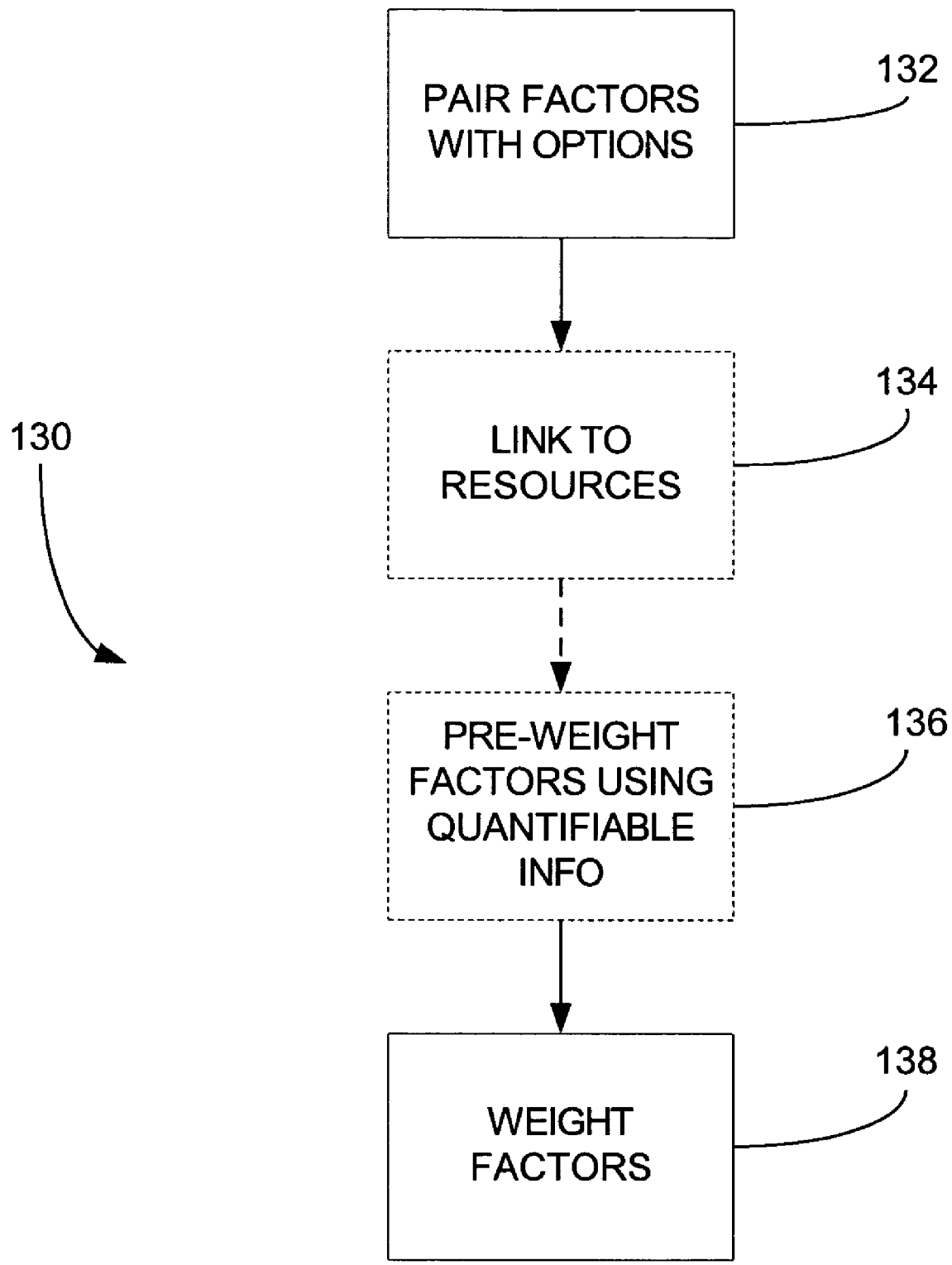
FIG. 4 is a detailed flow diagram of another aspect of the decision engine of FIG. 1 wherein the factors for each option are rated.

The sub-steps 132-138 of step 130, weighting the factors for each option, are illustrated in more detail in FIG. 4. Factors are paired with options in step 132, and each factor for each option is weighted by the user in step 138. In one embodiment, the user is instructed to "rate how much this factor supports your choice of this option", and is presented with a sliding scale that is movable using a mouse between the extremes of "not supportive" and "very supportive". Alternatively, other appropriate indicators of relative weight could be used. The user could be asked to weight each factor for each option, for example, from "poor" to "excellent". Depending on where the user places the scale, each factor will be assigned by decision engine 100 an integer score ranging from 0 (not supportive) to 10 (supportive). Alternatively, the user could simply be asked to numerically weight each factor on a scale from 1 to 10, or on any other useful or desired scale of scores.

Several optional steps may be provided to assist the user in weighting the factors. In step 134, resources may be provided such as on-line searches, links to manufacturer or other useful websites, studies, calculators, risk assessment calculators (for financial decisions, for example) and so on. The user may review such resources before weighting the factors in step 138. Additionally, in optional step 136, the factors may be pre-weighted based on known, quantifiable information. For example, if cameras having known sizes are being compared, the "size" factor for a larger camera may be pre-weighted to "not supportive" while the size factor for a smaller camera may be pre-weighted to "supportive" (or vice-versa, if the user desires a large camera). If clinical treatment options are being considered, the scale may be pre-weighted based on past clinical outcome data. The pre-weighting may be embodied as an initial, suggested positioning of the sliding scale, which the user would then be free to change if desired.

Step 4: Extra Effort (Optional)

Before computing and displaying the decision results in step 150, an "extra effort" step 140 may be provided for taking into account any extra effort that would have to be made for any of the options. If a car is being purchased, for example, an extra effort of "saving for a down payment" might be required, and this extra effort would be more significant for more expensive cars. For clinical treatment decisions, extra efforts of "cover insurance co-payment" or "take time off work" might be required.

Figure 5:
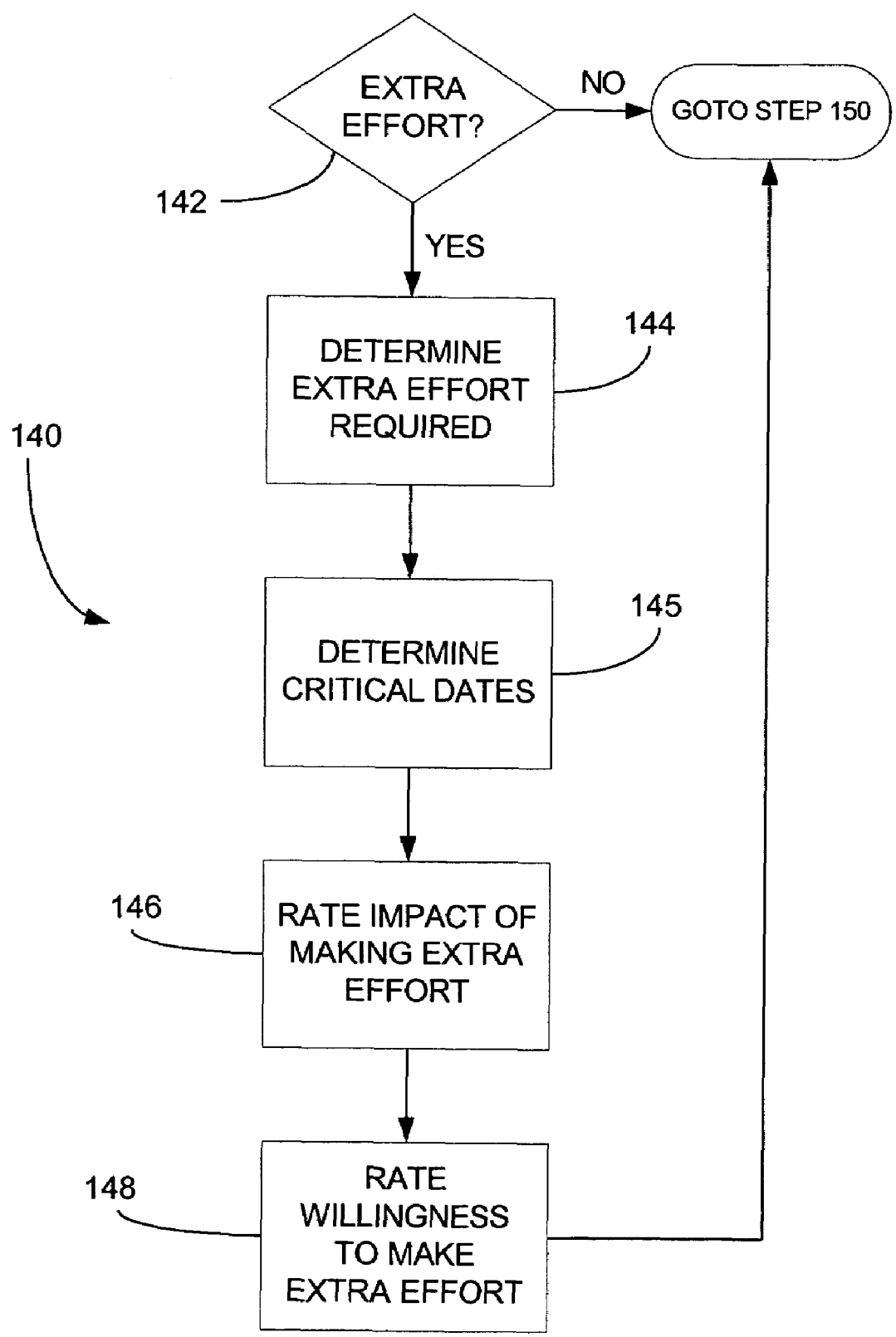
FIG. 5 is a detailed flow diagram of another aspect of the decision engine of FIG. 1 wherein any required extra effort is assessed.

The sub-steps 142-148 of step 140, assessing any extra effort that is required, are depicted in FIG. 5 for iterations of decision engine 100 that include this step. In step 142, the user is asked whether an extra effort is required. In one embodiment, the user simply has a choice between "yes" and "no". If the answer is "no", the extra effort steps are bypassed and the method proceeds directly to step 150 to conclude the decision results.

If the answer is "yes", in step 144, the user is asked what extra effort is required. This may be a free form response from the user, or a selection from a pull-down menu or the like. In step 145, the user is asked whether there are any critical dates associated with the extra effort. If, for example, the extra effort is completing a task by a certain date, the user would enter that date in step 145. In one embodiment, the user is presented with a calendar on which he can simply click the appropriate date.

In steps 146 and 148, the extra effort is rated on two scales. In step 146, the user is asked to rate the impact of making the extra effort, i.e., "how much impact would making the extra effort have in making the option possible?". In one embodiment, the user is presented with a sliding scale that is movable using a mouse between the extremes of "low impact" and "high impact". Alternatively, other appropriate indicators of the impact of making the extra effort could be used. The user could be asked to weight the benefit of making the extra effort, for example, from "not beneficial" to "very beneficial". Depending on where the user places the scale, the extra effort required will be assigned by decision engine 100 an integer score ranging from 0 (low impact) to 10 (high impact). Alternatively, the user could simply be asked to numerically rank the impact of the extra effort on a scale from 1 to 10, or on any other useful or desired scale of scores.

In step 148, the user is asked to rate his/her willingness to make the extra effort. In one embodiment, a sliding scale is used, with 0 being "not willing" and 10 being "very willing". Alternatively, other appropriate indicators of willingness or useful or desired scale of scores may be used.

It should be emphasized that step 140 is optional. While it provides a valuable contribution to the decision-making process, in streamlined versions of decision engine 100 intended solely to generate a very rapid comparison and decision, omission of step 140 may be desirable.

Step 5: Decision Results

In step 150 the options are ranked and displayed based on the user's input in the previous steps. In one implementation, the options are ranked and displayed in a "scorecard" format, wherein the importance, reason and weight behind each factor of each option, as well as any extra effort required for any of the options, is displayed to the user, providing the user with quantifiable knowledge that he has made the best decision based on all available options and associated factors. This empowers the user and enables him or her to make a confident purchase without being afflicted by the "buyers' remorse" that often accompanies a hasty or uninformed purchase decision.

Figure 6:
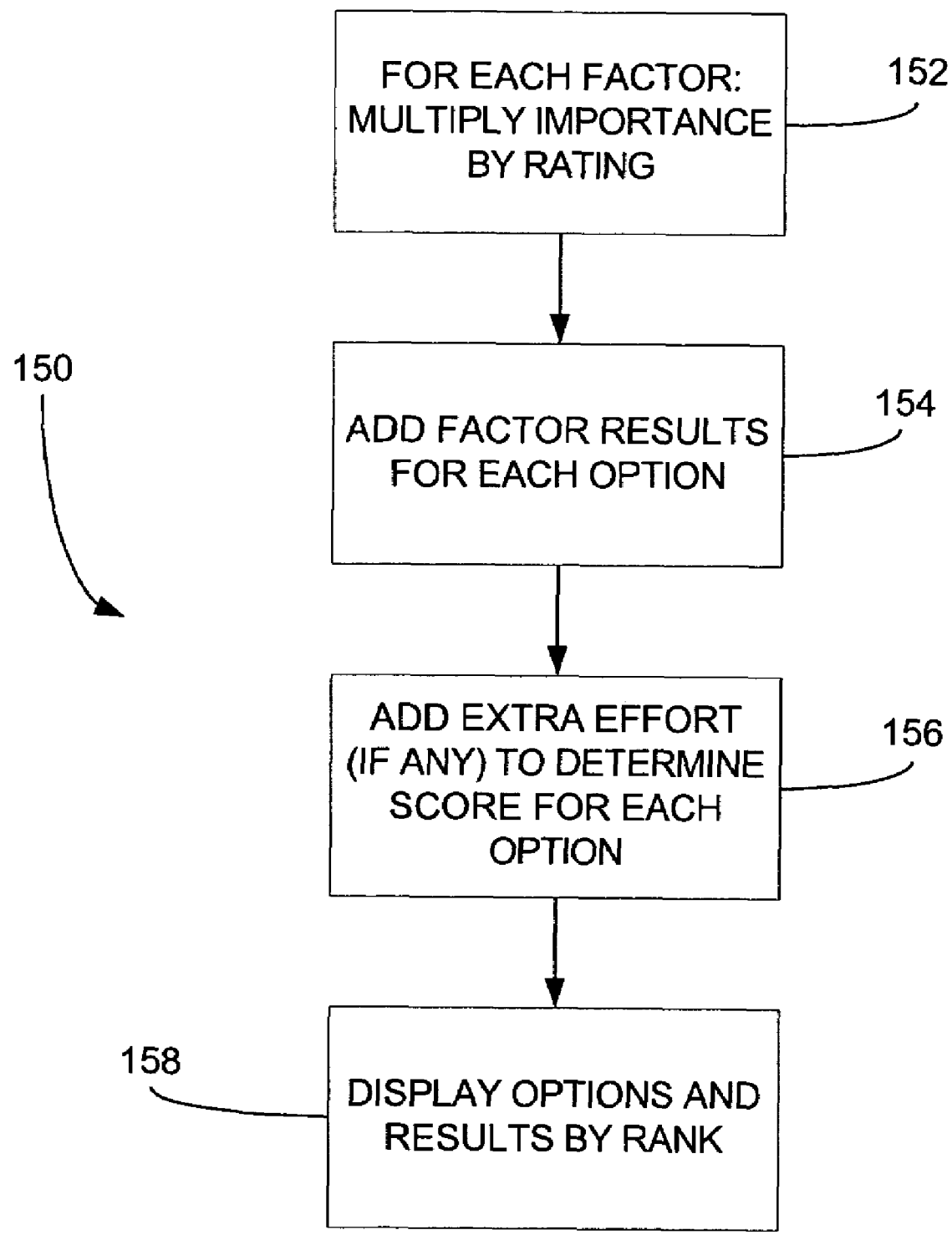
FIG. 6 is a detailed flow diagram of another aspect of the decision engine of FIG. 1 wherein the options are scored and ranked.

The sub-steps 152-158 of decision results step 150 are shown in FIG. 6. In step 152, for each factor of each option, the importance assigned to that factor (step 122) is multiplied by the weight assigned to that factor (step 138). The results for each factor of a given option are then added in step 154, to yield a factor sub-total for each option.

If the optional extra effort step 140 was not included, the factor sub-total for each option is the final score for that option, and the method proceeds directly to step 158 to display the options and results by rank (see below). If, however, the extra effort step 140 was included, the factor sub-totals are modified by the extra effort required. In one implementation, extra effort modifies the factor sub-totals as follows:

No extra effort. If, for a given option, no extra effort is required (per input of user in step 142), the factor sub-total is doubled to yield the final score for that option. If the factor sub-total was 100, for example, and no extra effort is required, the sub-total is doubled to yield a final score of 200 for that option.

Extra effort required. If for a given option, extra effort is required (per input of user in step 142), an extra effort component, determined by the user ratings of the impact of the extra effort and the willingness to make the extra effort, is added to the factor sub-total. The maximum value of the extra effort component is equal to the factor sub-total itself, and occurs when both the impact and willingness ratings are set to 10 (or the highest value of whatever scale is used). Hence, an option having a required extra impact with maximum impact and maximum willingness to make the effort will result in a doubling of the factor sub-score (effectively canceling out the 'extra effort' component of options requiring no extra effort). If the factor sub-total was 100, for example, and an extra effort is required having impact and willingness both rated as 10, the factor sub-total is doubled to yield a final score of 200 for that option.

Where an extra effort is required, and the impact and/or willingness ratings are somewhere between the extremes, each rating contributes a percentage of 50% of the factor sub-score, based on the rating. Consider, for example, a factor sub-score of 100, with an extra effort required, where the impact of making the effort has been rated as 8, and the willingness to make the effort has been rated as 6. The "impact" component is assigned 80% of 50% of the factor sub-total of 100, or (0.8)(50)=40. The "willingness" component is assigned 60% of 50% of the factor sub-total of 100, or (0.6)(50)=30. The impact and willingness components of the extra effort are then added to the factor sub-total to yield the final score for the factor. In this example, the final score after consideration of the extra effort is: 100 (factor sub-total)+40 (extra effort impact)+30 (extra effort willingness) =170.

In step 158, the options are ranked and displayed by score, showing the factors, reasons and importance/rating/extra effort for each factor of each option.

Consider, for example, a user who has selected laptop A, laptop B and laptop C as his options in a laptop purchase decision, and who has selected "size" and "performance" as his influencing factors. Size was rated as an importance of 9, for the reason "I travel frequently and need a compact laptop". Performance was rated as an importance of 5, for the reason that "I only use the laptop for basic functions like checking email and drafting simple documents". After reviewing the on-line links to resources and websites, the user assigned laptop A a size weighting of 3 and a performance weighting of 8; laptop B a size weighting of 6 and a performance weighting of 7; and laptop C a size weighting of 8 and a performance weighting of 5. Laptop A was not yet available for purchase, so it required an extra effort of "waiting for laptop to become available". The date the laptop becomes available, Jul. 1, 2004, was indicated as the critical date. The impact of making the extra effort (waiting) was assigned a 2 (not much impact), and the willingness to make the extra effort (waiting) was assigned a 3 (not very willing).

Based on this input, the option scores are computed as follows:

Laptop A

| | |
|---|---|
| Size: | Importance(9) * Weight(3) = 27 |
| Performance: | Importance(5) * Weight(8) = 40 |
| Factor Sub-total: | Size(27) + Performance (40) = 67 |
| Extra Effort: | Impact Component = 20% (2/10) of 50% of 67 = (.2)(.5)(67) = 6.7 |
| | Willingness Component = 20% of 50% of 67 = (.2)(.5)(67) = 6.7 |
| Final Score: | Factor Sub-Total(67) + Extra Effort Components (6.7 + 6.7) = 80.4 |

Laptop B

| | |
|---|---|
| Size: | Importance(9) * Weight(6) = 54 |
| Performance: | Importance(5) * Weight(7) = 35 |
| Factor Sub-Total: | Size(54) + Performance(35) = 89 |
| Extra Effort: | None |
| Final Score: | Factor Sub-Total doubled = 89 * 2 = 178 |

-continued

Laptop C

| | |
|---|---|
| Size: | Importance(9) * Weight(8) = 72 |
| Performance: | Importance(5) * Weight(5) = 25 |
| Factor Sub-Total: | Size(72) + Performance(25) = 97 |
| Extra Effort: | None |
| Final Score: | Factor Sub-Total doubled = 97 * 2 = 194 |

Hence, laptop C is ranked first with a score of 194, laptop B second with a score of 178, and laptop A a distant third with a score of 80.4. These rankings are presented in scorecard format to the user, with the factor importance, reasons and weights displayed to the user so that he/she can clearly see how the rankings were arrived at and how they correspond to issues of importance to him/her. Preferably, the user is also provided with the option to print the scorecard rankings for future reference.

In the example above, if the extra effort step were not included, the final scores would have simply been the factor sub-totals. The rankings would be the same, but closer: laptop C first with a score of 97, laptop B second with a score of 89, and laptop A third with a score of 67.

In a product decision-making application, optional steps may be provided to permit purchase of product options and/or accessories. Each option may be accompanied by, for example, an "add to cart" option, permitting a direct purchase or a link to the manufacturer's website for purchase. Additionally, he user may be presented with accessories that compliment the selected options. In one embodiment, the influencing factors chosen by the user, and importance/weights assigned to those factors, are used to identify and suggest accessories and/or additional products that would likely be of interest or use to the user.

Collection and Storage of Data

Another important aspect of the present invention is the ability to collect and store, in a database or the like, the data input by the user at each step of decision engine 100. The data is entered at a critical point in a user's life—the choice of a clinical treatment option or an expensive product purchase—and therefore provides real and valuable insight into purchase and decision patterns. For product purchase decisions, key and detailed information about consumer buying patterns and the factors of most importance in those patterns is obtained, which permits manufacturers to better tailor and target products based on the real needs and influencing factors of consumers.

The benefits provided by collecting and storing the data obtained during execution of decision engine 100 are also extremely significant in healthcare applications. Patients facing multiple options with no clear leader are able to access the decision-making criteria and input of previous patients facing similar options. Clinicians can access and use the data input by past patients in order to prospectively address anxieties and concerns of current patients. Researchers can derive insight into the concerns and factors driving treatment decisions so as to better tailor and direct future studies. Developers of devices and new therapies can benefit in the same manner.

Optional Steps for Developing an Action Plan

Figure 7:
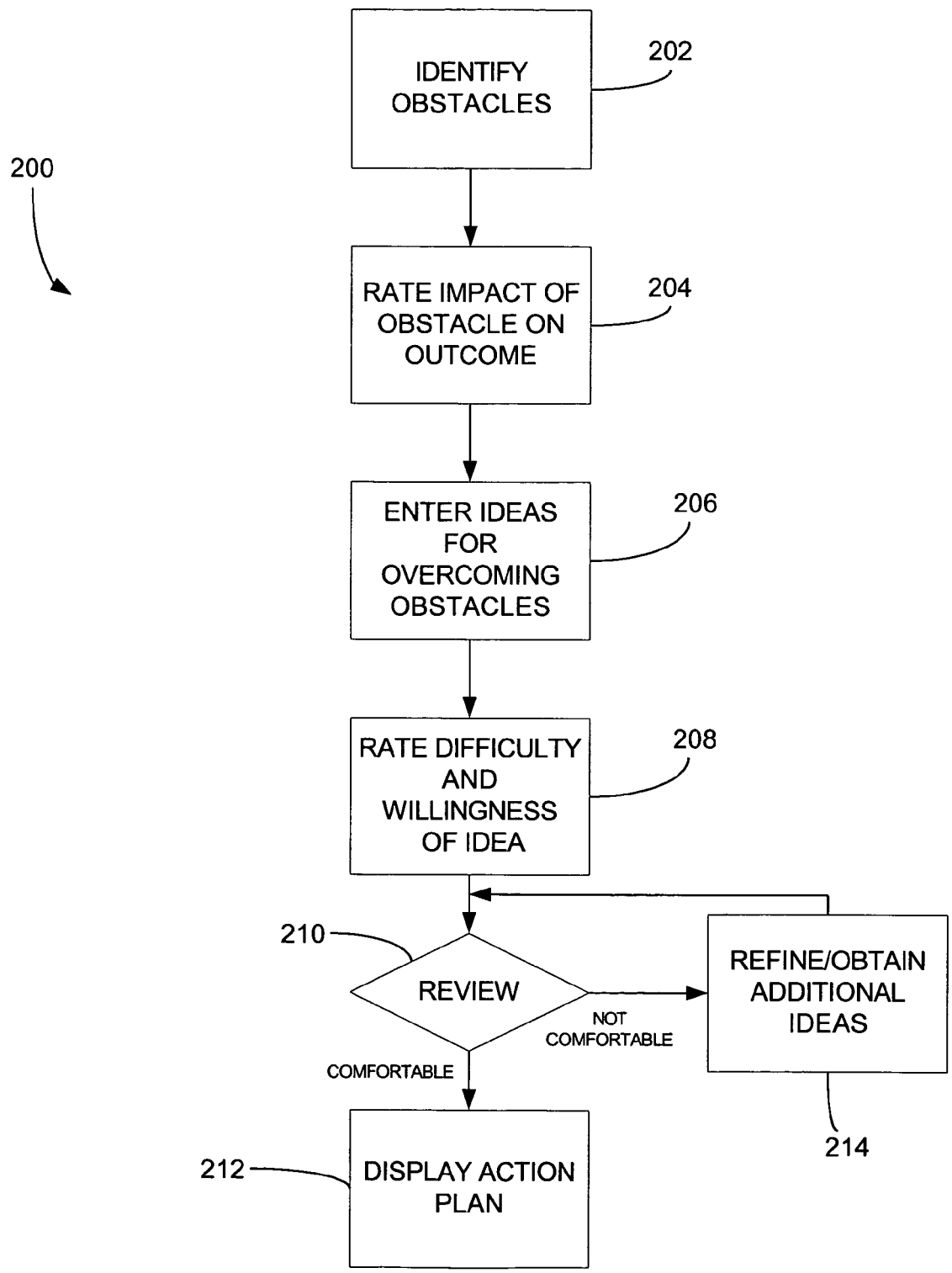
FIG. 7 is a flow diagram of a method for developing an action plan according to the present invention.

Decision engine 100 may stand alone for many applications. However, in another embodiment of the invention, the decision-making process of decision engine 100 is followed by additional steps for evoking creative ideas from the user and developing an action plan for making the chosen option a reality. FIG. 7 depicts additional steps in a method 200 for developing an action plan.

Optional Step 1: Identify Obstacles

In step 202, the user first identifies any obstacles standing in the way of making a selected option, such as the option identified as the best option by use of decision engine 100, a reality. For example, the user may be asked whether anything stands in the way of making the selected option a reality (yes/no) and, if so, to identify any such obstacles. For a car purchase, for example, the user may face the obstacle of "save for a down payment". In a clinical treatment scenario, obstacles may be lifestyle changes such as "need two weeks of nursing care" or "must find someone to cover my job for one month".

Obstacles may be entered by free form expression or by selection from a suggested list of common obstacles. Multiple obstacles may be identified. Obstacles may be drawn from a database or listing of suggested or common obstacles associated with the option or outcome in question.

Optional Step 2: Rate Obstacles

Each obstacle identified in step 202 is rated, in step 204, in terms of its impact on the outcome (i.e., its impact on the user's ability to make the option selected in the decision making process a reality). In one embodiment, the user is instructed to rate the level of impact the obstacle has on pursuing the selected option, and is presented with a sliding scale that is movable using a mouse between the extremes of "minor obstacle" and "major obstacle". Alternatively, other appropriate indicators of relative impact of the obstacle could be used. Depending on where the user places the scale, the obstacle is assigned by decision engine an integer score ranging from 0 (minor obstacle) to 10 (major obstacle). Alternatively, the user could simply be asked to numerically rate the impact of the obstacles on a scale from 1 to 10, or on any other useful or desired scale of scores.

Optional Step 3: Creative Ideas for Overcoming Obstacles

In step 206, the user is asked to think of and enter creative ideas for overcoming the obstacles or meeting the requirements. Entries here will typically be free form expression, however, a suggested list of ideas from a pull-down menu or the like may also be provided to assist the user. Continuing the examples above, where the user is seeking to purchase a car and faces the obstacle of saving for a down payment, he/she might enter the creative idea of "get a weekend job" for overcoming the obstacle. For clinical treatment applications, "temporarily move in with son" may be a creative idea for overcoming the obstacle of finding nursing care, and "do some work from home" may be a creative idea for overcoming the obstacle of being away from the job for some time.

In one embodiment, the user is also asked whether there are any applicable critical dates, and is provided with a calendar to identify any such dates. If there are applicable critical dates, the user is asked to assess the likelihood that the obstacle will be overcome by the critical date. In one embodiment, the user selects between "likely" or not "likely". Alternative means for rating the likelihood of overcoming the obstacle by the critical date may be provided such as, for example, sliding scales as discussed herein.

Optional Step 4: Rate Creative Ideas

In step 208, the creative ideas evoked from the user are evaluated by the user based on their difficulty level and the user's willingness to act on the idea. In one embodiment, the ideas are rated on two sliding scales: first, based on their difficulty to implement (from "not difficult" to "very difficult"); and second, based on the user's willingness to act (from "not willing" to "very willing"). Alternatively, other appropriate indicators of the difficulty of and willingness to act on the idea could be used. Depending on where the user places the scale, the willingness and difficulty associated with each creative idea will be assigned an integer score ranging from 0 (low difficulty/willingness) to 10 (high difficulty/willingness). Alternative rankings or scales of these factors may be used.

Optional Step 5: Review Ideas/Obstacles

In step 210, a summary of the obstacles, creative ideas for overcoming the obstacles and any associated critical dates, and the difficulty of and willingness to act on the ideas is displayed to the user. In one embodiment, the user is asked to indicate whether he/she is comfortable with the obstacles and ideas for overcoming the obstacles as they stand or, alternatively, whether he/she would like to search for further ways to make implementing the ideas and overcoming the obstacles easier and more effective. If the user is comfortable with the ideas/obstacles in their current form, the method proceeds to step 212, for generation and display of an action plan. If the user is not comfortable, and feels that further analysis of ways to implement the ideas and to overcome the obstacles is required, the method proceeds to step 214.

In another embodiment, based on the input of the user, including the difficulty and willingness to act ratings obtained in step 208, a suggestion may be presented to the user regarding the decision in step 210. If the user has indicated, for example, that the ideas are not difficult to implement and that he/she is very willing to act on them, then it may be suggested that the user proceed directly to step 212 for generation and display of an action plan without further input or analysis. Conversely, if the ideas are difficult and/or the user is not willing to act on them, the method may suggest the need for further analysis and thought (i.e., proceed to step 214). This suggestion may be based on, for example, multiplication of the "difficult" and "willingness" factors and comparison of the result to a pre-determined threshold. In still another embodiment, the method may automatically proceed to either step 212 or step 214 based on analysis of the user input. That is, the user may not be given an option to see an action plan until the ideas for overcoming the obstacles are judged to meet some threshold of likelihood of success.

Optional Step 6: Refine or Obtain Additional Ideas to Reduce Risk

If the method has proceed by choice of the user or automatically to step 214, further creative ideas for reducing risk and enhancing the chances of overcoming the obstacles are elicited from the user. For each previously entered creative idea, for example, the user may be asked for additional ideas in making the original idea more effective or easier to execute. Consider, for example, a user facing the obstacle of saving for a down payment for a car, who has offered the creative idea of getting a weekend job, but has arrived at step 214 because he has given the idea a high difficulty rating assessed his willingness to act on the idea as low. In this scenario, the user may enter the additional idea of "do yard work for parents" as one that it is easier and he is more likely to implement. In clinical treatment applications, additional ideas may include "have family rotate visits at home, so as to not have to actually make a move", where the initial idea of moving in with son had too high of a difficulty/willingness rating. As another example, where working from home had a high difficulty/willingness rating, an additional creative idea evoked from the user at this step might be "set up weekly conference calls with the office so as to reduce stressful time on computer".

Again, the user may enter associate critical dates. In one embodiment, the user may rate the difficulty and willingness of the new idea on sliding or other appropriate scales.

After step 214, in the embodiment of FIG. 7, the method proceeds back to step 210 for further review. This "drill down" approach to elicitation of creative ideas may continue until the user has generated creative ideas with acceptable likelihood of success and risk reduction. Alternatively, the method could proceed directly to step 212 for generation and display of an action plan without further review/analysis.

Optional Step 7: Generate and Display Action Plan

In step 212, an action plan is presented to the user based on his input. The selected decision option and scorecard may be re-displayed, as described with respect to step 150. Then, an action plan for making the selected decision option a reality may be generated and displayed. This will include obstacles to overcome, the ideas for overcoming the obstacles, and the critical dates by which such ideas must be completed. The difficulty and willingness ratings are also preferably displayed. The user now has a robust analysis of his decision-making process, as well as the actions and timeline necessary to implement that decision. He/she has a clear understanding of the situation at hand and the necessary steps necessary to implement his/her decision.

In one embodiment, the user is provided with the option to print the action plan and/or download the action plan to a mobile communication or storage device. Additionally, the opportunity to explore and create action plans for secondary options may also be provided. Should the user wish to explore secondary options (i.e. options considered by decision engine 100 but not selected as the primary option), method 200 would simply be repeated for such options. Following generation and display of the action plan, the user may also be presented with appropriate resources and/or links to information for further study of the topic/decision at hand.

While various embodiments of the invention have been described, it will be apparent to those of ordinary skill in the art that many more embodiments and implementations are possible that are within the scope of this invention.

What is claimed is:

1. A method for decision-making implemented as a computer program in a computer-readable storage medium comprising:

obtaining options to be considered for the outcome of a decision;

obtaining influencing factors in making the decision;

obtaining a non-preprogrammed rating of the importance of each of the influencing factors from a user of the computer program;

obtaining a weighting of each of the influencing factors for each of the options; and computing and displaying a ranking of the options.

2. A method as claimed in claim 1, wherein the options comprise products for potential purchase.

3. A method as claimed in claim 1, wherein the options comprise clinical treatment pathways.

4. A method as claimed in claim 1, and further comprising:

obtaining a reason that each of the influencing factors is important.

5. A method as claimed in claim 1, and further comprising:
providing resources to assist a user in weighting the influencing factors.

6. A method as claimed in claim 1, and further comprising:
pre-weighting the influencing factors based on known, quantifiable information about the influencing factors.

7. A method as claimed in claim 1, and further comprising:
assessing whether extra effort is needed for any of the options.

8. A method as claimed in claim 7, and further comprising:
obtaining the needed extra effort, the impact of making the effort, and the willingness to make the effort.

9. A method as claimed in claim 8, and further comprising:
obtaining any critical dates associated with the extra effort.

10. A method as claimed in claim 1, wherein the ranking of options is computed by multiplying the importance and weight of each factor, and adding the results for each option.

11. A method as claimed in claim 10, wherein the rankings are displayed to the user in a scorecard format.

12. A method as claimed in claim 8, wherein the ranking of options is computed by multiplying the importance and weight of each factor, adding the results for each option and, if extra effort was required, modifying the result based on the extra effort.

13. A method as claimed in claim 2, and further comprising:
providing the ability to purchase products and accessories based on the user's options, influencing factors, and ratings and weights assigned to those factors.

14. A method as claimed in claim 1, and further comprising:
collecting and storing data input by multiple users to facilitate analysis of decision-making patterns and factors.

15. A method as claimed in claim 1, and further comprising:
developing an action plan for making a chosen option a reality.

16. A method as claimed in claim 15, wherein the steps for developing an action plan comprise:
obtaining obstacles standing in the way of making the chosen option a reality;
obtaining ratings of the impact of the obstacles on making the chosen option a reality;
obtaining creative ideas for overcoming the obstacles;
determining risk by obtaining ratings of the user's difficulty to implement the creative ideas and the user's willingness to implement the creative ideas;
obtaining additional creative ideas if it is necessary to reduce the risk; and
generating and displaying an action plan based on the chosen option, the obstacles and the creative ideas for overcoming the obstacles.

17. A computer program product comprising a computer readable storage medium having computer instructions stored therein for assisting a user in making a purchase decision, the computer program product comprising instructions for:
obtaining a selection of products to be considered for purchase;
obtaining a selection of influencing factors in the purchase;
obtaining a rating of the importance of each of the influencing factors;
obtaining a reason that each of the influencing factors is important;
obtaining a weighting of the factors for each option, and providing resources to assist the user in the weighting;
computing and displaying a ranking of the products by multiplying the importance of each factor by its weighting and adding the results for each of the options; and
providing the option to purchase the products.

18. A computer program product as claimed in claim 17, and further comprising:
collecting and storing the input of multiple users for use in analyzing consumer buying patterns and in tailoring and targeting products based on those patterns.

19. A computer program product comprising a computer readable storage medium having computer instructions stored therein for assisting a patient in making a clinical treatment decision, the computer program product comprising instructions for:
obtaining a selection of clinical treatment options to be considered;
obtaining a selection of influencing factors in the choice of options;
obtaining a rating of the importance of each of the influencing factors;
obtaining a reason that each of the influencing factors is important;
obtaining a weighting of the factors for each option, and providing resources to assist the user in the weighting; and
computing and displaying a ranking of the clinical treatment options by multiplying the importance of each factor by its weighting and adding the results for each of the options.

20. A computer program product as claimed in claim 19, and further comprising:
collecting and storing the input of multiple patients for use by clinicians in prospectively addressing concerns of other patients, for use by researchers in better tailoring and directing future studies, and for use by developers of new devices and therapies.

* * * * *